United States Patent [19]

Ikesu et al.

[11] Patent Number: 5,658,720
[45] Date of Patent: Aug. 19, 1997

[54] PHOTOGRAPHIC MATERIAL CONTAINING CYAN COUPLER

[75] Inventors: Satoru Ikesu; Mitsuhiro Fukuda; Vladimir F. Rudchenko; Yutaka Kaneko, all of Hino, Japan

[73] Assignee: Konica Corporation, Japan

[21] Appl. No.: 570,324

[22] Filed: Dec. 11, 1995

[30] Foreign Application Priority Data

Dec. 15, 1994 [JP] Japan .................................. 6-333366

[51] Int. Cl.$^6$ ...................................................... G03C 7/38
[52] U.S. Cl. ............................................................ 430/558
[58] Field of Search ....................................... 430/558, 567

[56] References Cited

U.S. PATENT DOCUMENTS 5,342,749  8/1994  Sakonoue ................................ 430/558

FOREIGN PATENT DOCUMENTS

| 0287265 | 10/1988 | European Pat. Off. . |
| 1106057 | 4/1989 | Japan . |
| 1118132 | 5/1989 | Japan ...................................... 430/558 |
| 1167840 | 7/1989 | Japan . |
| 1172956 | 7/1989 | Japan ...................................... 430/558 |

OTHER PUBLICATIONS

European Search Report EP 95 30 9134.

*Primary Examiner*—Lee C. Wright
*Attorney, Agent, or Firm*—Jordan B. Bierman; Bierman, Muserlian and Lucas LLP

[57] ABSTRACT

A silver halide photographic light sensitive material comprising a support having thereon a silver halide emulsion layer containing a cyan dye-forming coupler represented by the following formula (I) or (II).

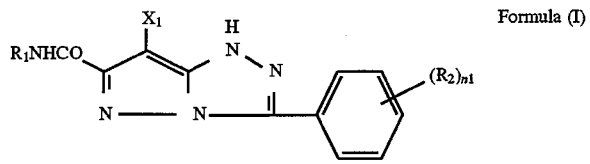

Formula (I)

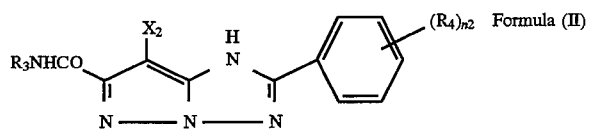

Formula (II)

3 Claims, No Drawings

PHOTOGRAPHIC MATERIAL CONTAINING CYAN COUPLER

FIELD OF THE INVENTION

The present invention is related a silver halide color photographic light sensitive material containing a cyan coupler and particularly to a photographic cyan coupler improved in dye forming property and color reproduction.

BACKGROUND OF THE INVENTION

As cyan dye image forming couplers, there have been known phenols and naphthols.

However, a cyan dye image obtained from the phenols or naphthols known in the art has a problem in color reproduction. Thus, it has an unsharp absorption form in a shorter wave length range, further having an unwanted absorption, i.e., asymmetric absorption in a green wavelength region. Accordingly, in a negative film, correction for the asymmetric absorption must be made by means of masking; in a color paper, however, there is no means for the correction so that it deterirates color reproduction.

Furthermore, the dye image obtained from the phenols and naphthols known in the art has still problems in storage stability thereof. Thus, a dye image obtained from a 2-acylaminophenol cyan coupler as disclosed in U.S. Pat. Nos. 2,367,531 and 2,423,730 was found to be inferior in heat fastness. A dye image obtained from a 2,5-diacylaminophenol cyan coupler as disclosed in U.S. Pat. Nos. 2,369,929 and 2,772,162 was inferior in light fastness and a dye image obtained from a 1-hydroxy-2-naphthamide cyan coupler was generally insufficient in light and heat fastness.

A 2,5-diacylaminophenol cyan coupler as disclosed in U.S. Pat. No. 4,122,369 and JP-A 57-155538 (1982) (the term "JP-A" means an "unexamined published Japanese patent application) and 2,5-diacylaminophenol cyan coupler having a hydroxy group within a ballast group, as disclosed in U.S Pat. No. 3,880,661 have not achieved sufficiently satisfactory level in the light and heat fastness and yellow stain occurred during the prolonged storage of the dye image.

For the purpose of solving these problems, there was proposed pyrazoloazole type cyan coupler as disclosed in JP-A 64-554 (1989), 63-250649 (1988) and 63-250650 (1988).

An electron-withdrawing group and a group capable of hydrogen-bonding were introduced into each of these couplers so as to satisfy an absorption wavelength of a dye formed, so that good color reproduction was attained. However, coupling activity did not reach a sufficiently satisfactory level, so that dye forming property and color reproduction could not be satisfied simultaneously.

In view of these conditions, the inventors of the present invention have made studies broadly and succeeded to find out pyrazoloazole type cyan coupler having improved color reproduction and excellent dye forming property.

SUMMARY OF THE INVENTION

Accordingly, an object of the present invention is to provide a cyan dye-forming coupler for use in a silver halide color photographic light sensitive material, which is superior in dye formation to form a vivid, cyan color image having a sufficiently high density and an absorption with a sharp edge and little secondary absorption in a blue and green region, socalled, being excellent in spectral absorption characteristics.

Further, another object of the invention is to provide a photographic cyan dye-forming coupler capable of forming a cyan dye image which causes no hue change against heat and light.

The above objects of the invention can be accomplished by a silver halide photographic light sensitive material containing a cyan coupler represented by the following formula (I) or (II).

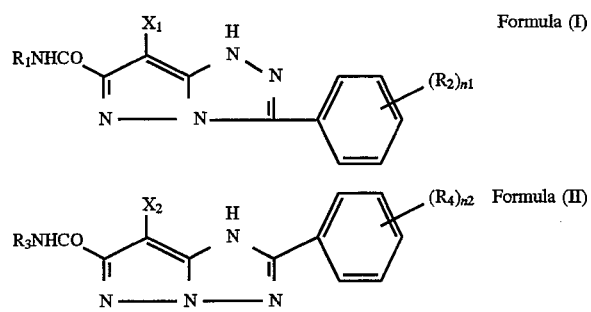

In the formula, $R_1$ and $R_3$ represents a substituted alkyl group or a cycloalkyl group; $R_2$ and $R_4$ represents a hydrogen atom or a substituent; $X_1$ and $X_2$ represent a hydrogen atom or a group capable of being leaving upon reaction with an oxidation product of a color developing agent; and $n_1$ and $n_2$ are each an integer of 1 to 5.

DETAILED EXPLANATION OF THE INVENTION

First, with regard to a compound represented by formula (I) or (II), detailed explanation is provided. $R_1$ and $R_3$ independently represent a substituted alkyl group or a cycloalkyl group. The alkyl group has preferably 1 to 32 carbon atoms, which may be branched or unbranched. As examples of the unbranched alkyl group are cited methyl, ethyl, propyl, octyl and decyl. The branched alkyl group includes iso-propyl or tert-butyl. The substituent of $R_1$ or $R_3$ is not limitative but representative examples thereof include an alkyl group (preferably, having 1 to 32 carbon atoms) aryl group, anilino group, acylamino group, sulfonamide group, alkylthio group, arylthio, alkenyl and cycloalkyl group. Furthermore are cited a halogen atom, cycloalkenyl group, alkynyl group, heterocyclic group, sulfonyl group, sulfinyl group, phosphonyl group, acyl group, carbamoyl group, sulfamoyl group, cyano group, alkoxy group, aryloxy group, heterocyclic-oxy group, siloxy group, acyloxy group, sulfonyloxy, carbamoyloxy group, amino group, alkylamino group, imido group, ureido group, sulfamoylamino group, alkoxycarbonylamino, aryloxycarbonylamino group, alkoxycarbonyl group, aryloxycarbonyl group, heterocyclic-thio group, thioureido group, carboxy group, hydroxy group, mercapto group, nitro group, sulfo group, spiro-compound residue and bridged hydrocarbon compound residue.

$R_1$ or $R_3$ is also a cycloalkyl group such as cyclohexyl, which may have a substituent. The substituent is the same as in the case when $R_1$ or $R_3$ is a substituted alkyl group.

A substituent represented by $R_2$ and $R_4$ of formula (I) and (II) is not limitative but as representative examples thereof are cited an alkyl group, aryl group, anilino group, acylamino group, sulfonamide group, alkylthio group, arylthio, alkenyl and cycloalkyl group. Furthermore are cited a halogen atom, cycloalkenyl group, alkynyl group, heterocyclic group, sulfonyl group, sulfinyl group, phosphonyl group, acyl group, carbamoyl group, sulfamoyl group, cyano group, alkoxy group, aryloxy group, heterocyclic-oxy group, siloxy group, acyloxy group, sulfonyloxy, carbamoyloxy group, amino group, alkylamino group, imido group, ureido group, sulfamoylamino group, alkoxycarbonylamino, aryloxycarbonylamino group, alkoxycarbonyl group, aryloxycarbonyl group, heterocyclic-thio group, thioureido group, carboxy group, hydroxy-group, mercapto group, nitro group, sulfo group, spiro-compound residue and bridged hydrocarbon compound residue.

With regard to the group represented by $R_2$ or $R_4$, an alkyl group is preferably one having 1 to 32 carbon atoms, which may be branched or unbranched.

An aryl group is preferably a phenyl group.

As an acylamino group is cited an alkylcarbonylamino group or arylcarbonylamino group.

As a sulfonamide group is cited an alkylsulfonylamino group or arylsulfonylamino group.

An alkyl moiety and an aryl moiety in an alkylthio group and arylthio group are respectively the same as an alkyl group and aryl group represented by $R_2$ and $R_4$ described above.

An alkenyl group has preferably 2 to 32 carbon atoms, and as a cycloalkyl group is preferably one having 3 to 12 carbon atoms, more preferably, 5 to 7 carbon atoms. An alkenyl group may be branched or unbranched.

A cycloalkenyl group has preferably 3 to 12 carbon atoms, more preferably, 5 to 7 carbon atoms. There are cited a sulfonyl group such as a alkylsulfonyl group or arylsulfonyl group; a sulfinyl group such as a alkylsulfinyl group or arylsulfinyl group; a phosphonyl group such as an alkylphosphonyl group, alkoxyphosphonyl, aryloxyphosphonyl group or arylphosphonyl group; an acyl group such as an alkylcarbonyl group or arylcarbonyl group; a carbamoyl group such as an alkylcarbamoyl group or arylcarbamoyl group; a sulfamoyl group such as an alkylsulfamoyl group or arylsulfamoyl group; an acyloxy group such as an alkylcarbonyloxy group or arylcarbonyloxy group; a sulfonyloxy group such as an alkylsulfonyloxy or arylsulfonyloxy group; a carbamoyloxy group such as an alkylcarbamoyloxy group or arylcarbamoyloxy group; a ureido group such as an alkylureido group or arylureido group; a sulfamoylamino group such as an alkylsulfamoylamino group or arylsulfamoylamino group; a heterocyclic group, which is preferably 5, 6 or 7-membered cycle, such as a 3,4,5,6-tetrahydropyranyl-2-oxy group or 1-phenyltetrazole-5-oxy group; a heterocyclic-thio group, which is preferably 5 to 7-membered one, such as a 2-pyridylthio group, 2-benzothiazolylthio group, 2,4-diphenoxy-1,3,5-triazole-6-thio group; a siloxy group such as a trimethysiloxy group, triethylsiloxy group or dimethylbutylsiloxy group; an imido group such as a succinimido group, 3-heptadecylsuccinimido group, phthalimido group or glutarimido group; a spiro compound residue such as spiro[3, 3]heptane-1-yl; and a bridged hydrocarbon compound residue such as bicyclo[2,2,1]heptane-1-yl, tricyclo[3,3,1,1$^{37}$] decane-1-yl or 7,7-dimethyl-bicyclo[2,2,1]heptane-1-yl.

The above groups may be substituted by a ballast group such as long-chained hydrocarbon group or polymer residue.

In formulas (i) and (II), $n_1$ and $n_2$ are each an integer of 1 to 5, provided that, when $n_1$ or $n_2$ is 2 or more, $R_2$ and $R_4$ may be the same with or different from each other.

A group capable of leaving upon reaction with an oxidation product of a developing agent, as represented by X includes a halogen atom (a chlorine, bromine and fluorine atom), alkylene group, alkoxy group, aryloxy group, heterocyclic-oxy group, acyloxy group, sulfonyloxy group, alkoxycarbonyloxy group, aryloxycarbonyl group, alkyloxalyloxy group, alkoxyoxalyloxy group, alkylthio, arylthio group, heterocyclic-thio group, alkyloxythiocarbonylthio group, acylamino group, sulfonamide group, nitrogen-containing heterocyclic group having a bond at the nitrogen atom (i.e., it connects an other group through the nitrogen atom), alkyloxycarbonylamino group, aryloxycarbonylamino group, and carboxy group. Among these are preferable a hydrogen atom, halogen atom, alkoxy group, aryloxy group, heteroyclicioxy group, alkylthio group, arylthio group, heterocyclic-thio group and nitogen-containing heterocyclic group.

Among compounds represented by formula (i) and (II), is preferable a compound represented by formula (I) from the point of color reproduction.

Examples of compounds represented by formula (I) or (II) are shown as below but the present invention is not limited thereto.

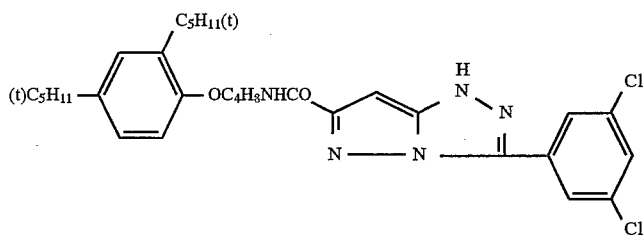

(1)

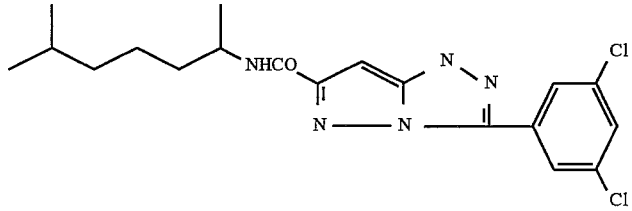

(2)

-continued
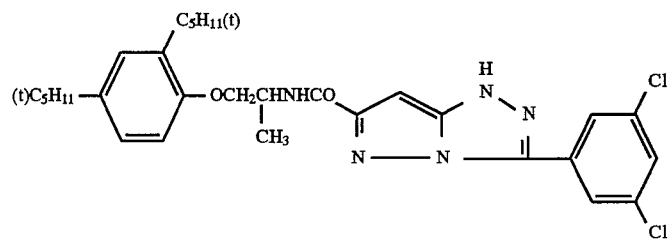
(3)
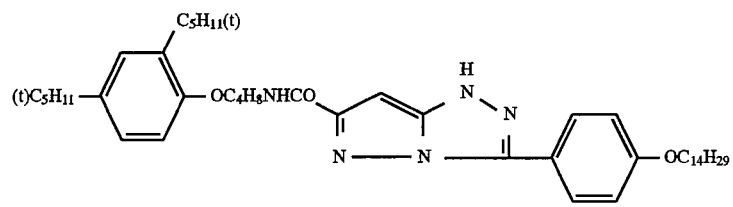
(4)
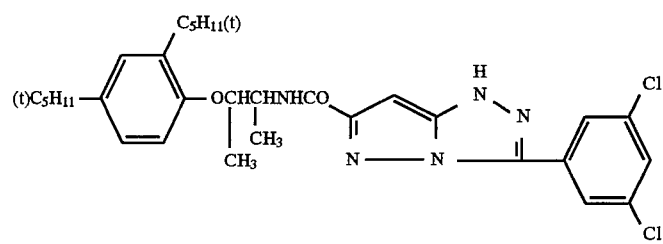
(5)
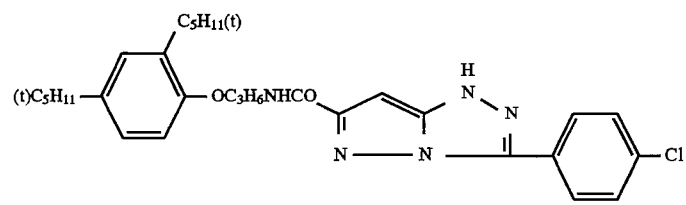
(6)
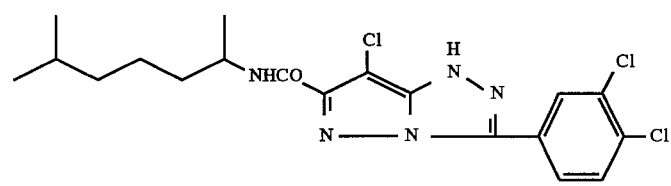
(7)
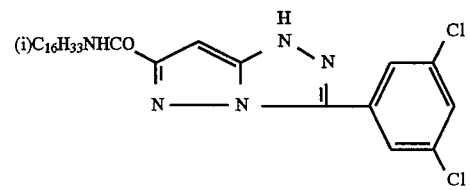
(8)
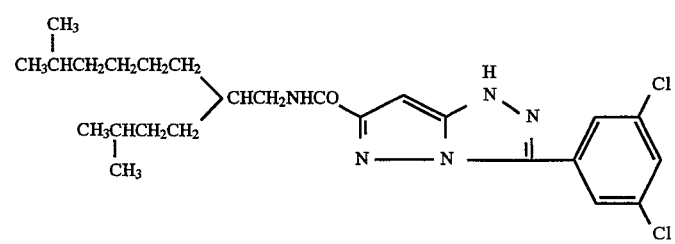
(9)

-continued
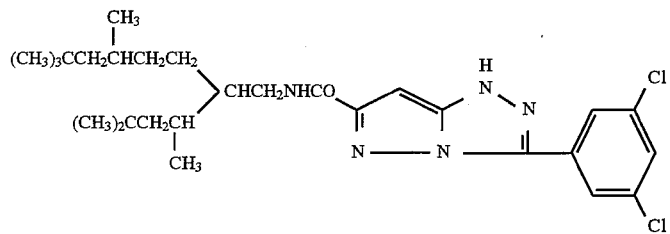
(10)
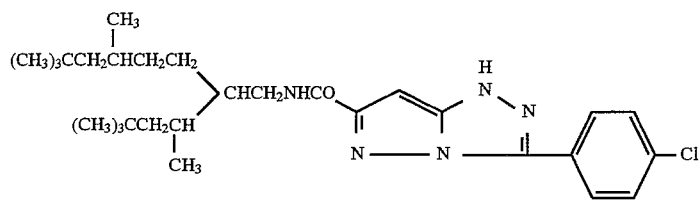
(11)
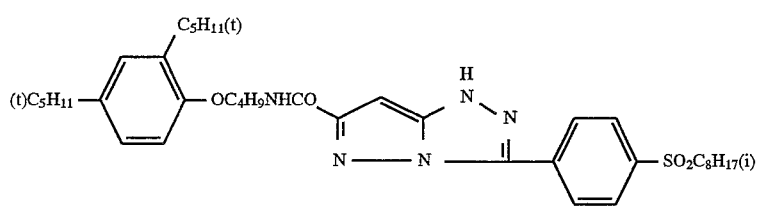
(12)
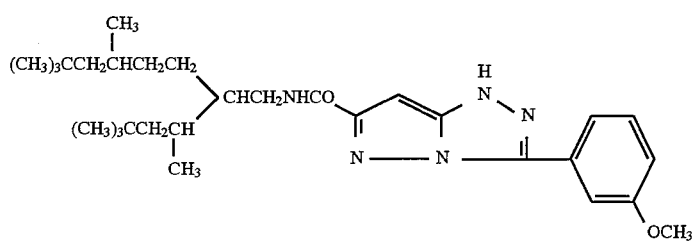
(13)
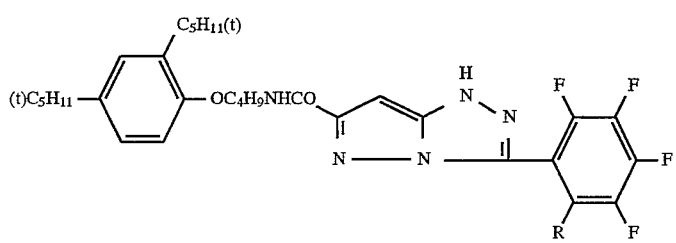
(14)
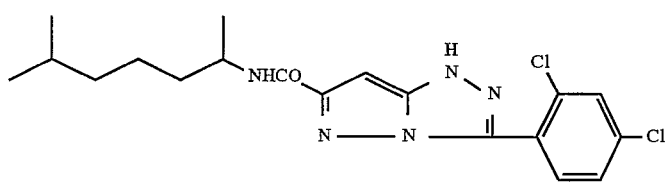
(15)
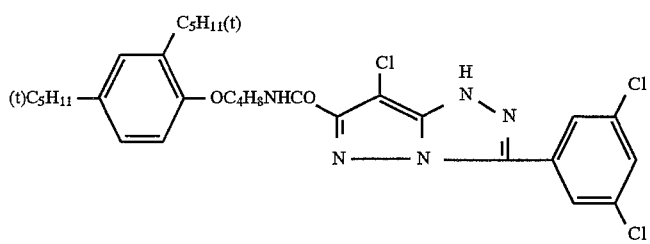
(16)

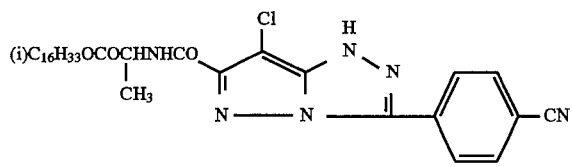
(17)
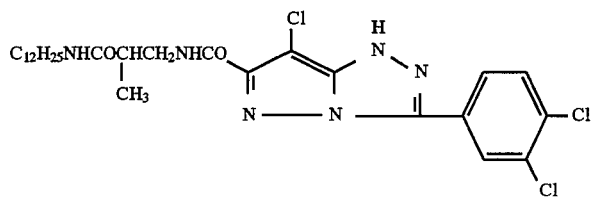
(18)
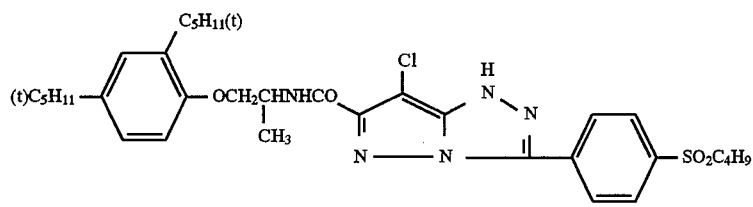
(19)
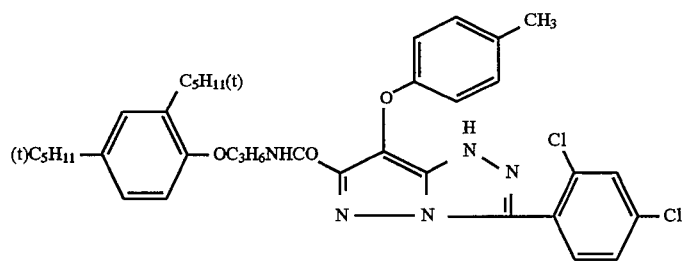
(20)
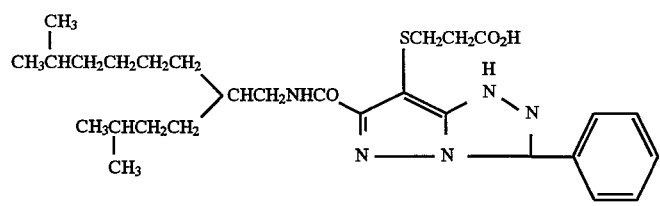
(21)
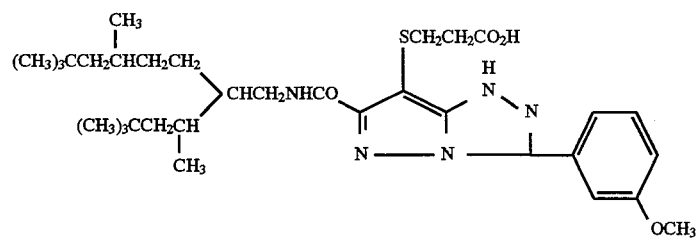
(22)
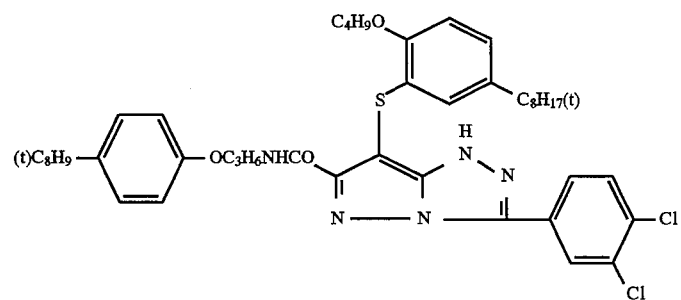
(23)

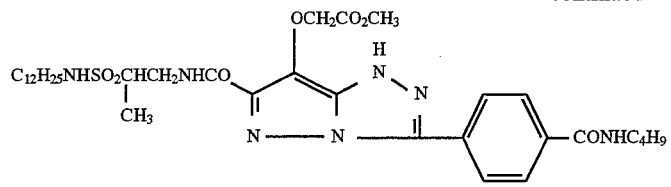
(24)
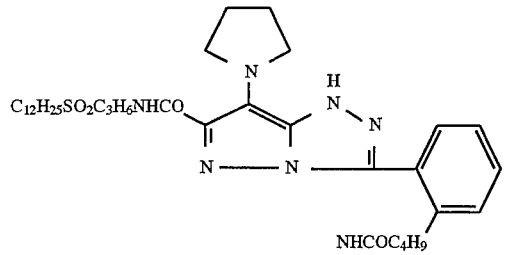
(25)
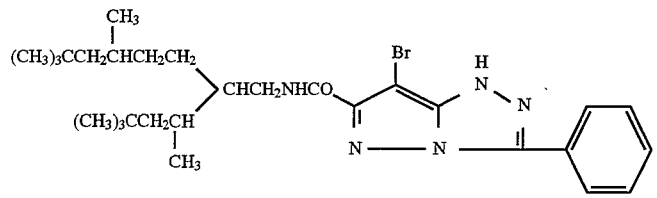
(26)
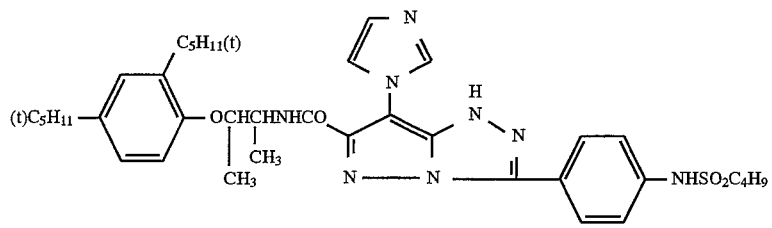
(27)
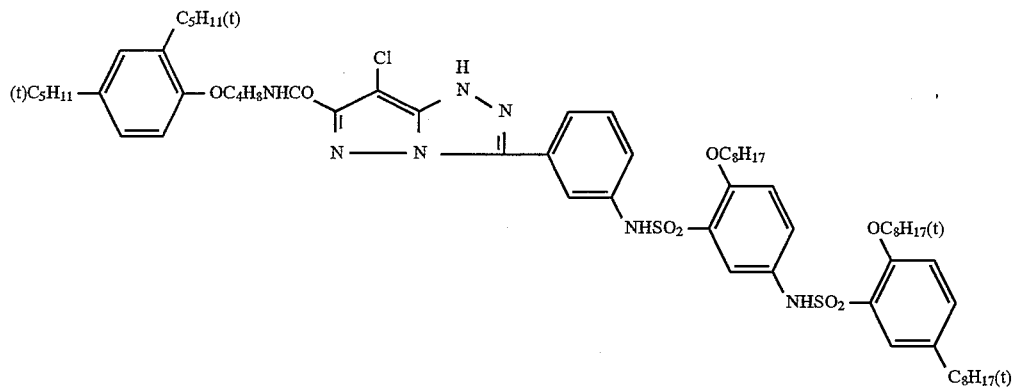
(28)
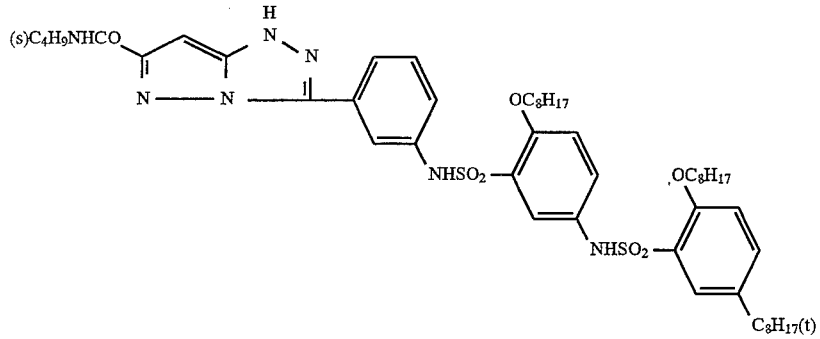
(29)

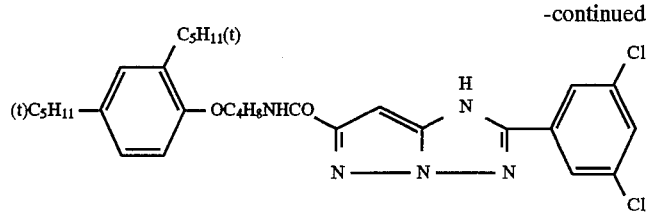
(30)

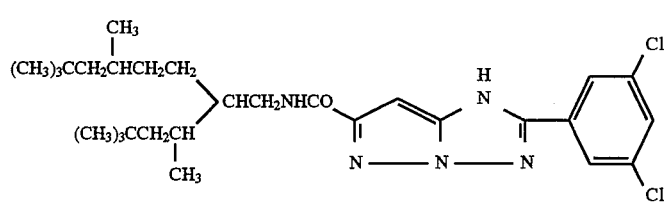
(31)

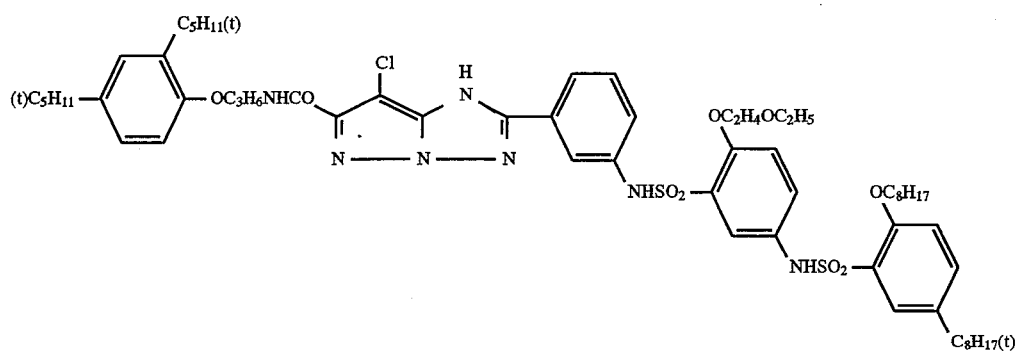
(32)

(33)

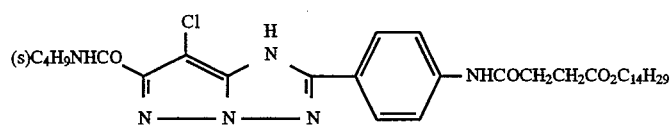

Synthesis examples
Synthesis of exemplified Compound (1)
Compound (1) was synthesized according to the following scheme.

pound (1b) of 54.6 g (0.280 mol) at room temperature. The mixture was heated under reflux for 9 hrs. After completing the reaction, the reaction mixture was allowed to stand to be

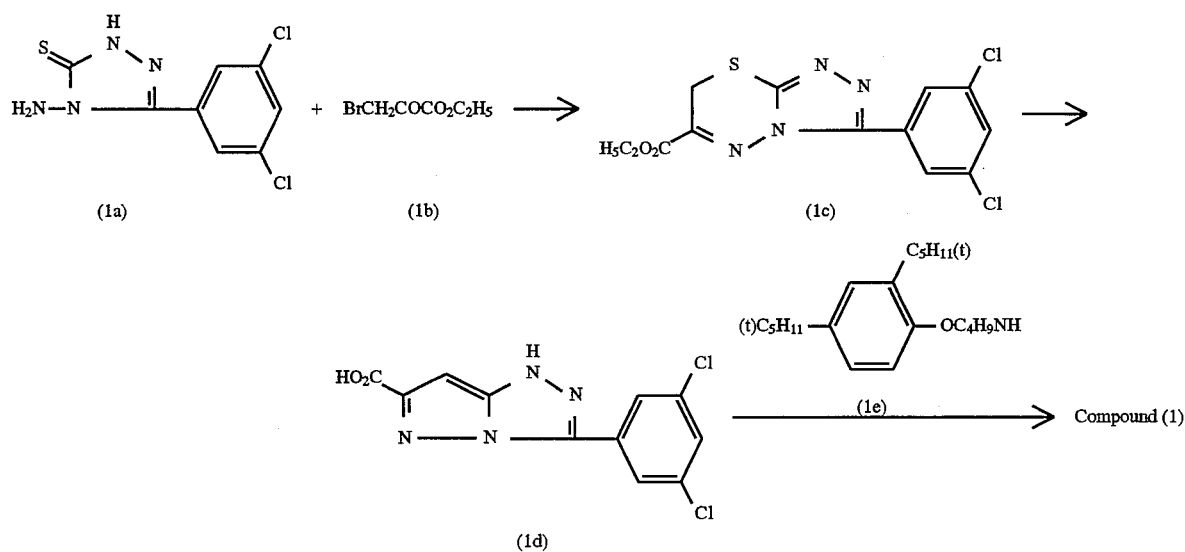

i) Synthesis of Intermediate (1c)
Compound (1a) of 69.8 g (0.267 mol) was dispersed in 500 ml of ethanol and thereto was dropwise added a comcooled and precipitated crystals were filtered off to obtain an intermediate (1c) of 85.5 g in a 89.4% yield.

ii) Synthesis of Intermediate (1d)

Compound (1c) of 85.5 g (0.239 mol) was heated with anhydrous acetic acid of 250 ml under reflux for 3.5 hrs. After completing the reaction, anhydrous acetic acid was distilled away. Thereafter, acetic acid of 580 ml, concentrated hydrochloric acid of 127 ml and 32–36% hypophosphorous acid of 30 ml were added thereto and the mixture was reacted for 4 hrs. at 100° C. After completing the reaction, precipitated crystals were filtered off and washed with acetonitrile and then with hexane to obtain Intermediate (1d) of 60.8 g in a 85.6% yield.

iii) Synthesis of exemplified Compound (1)

Intermediate (1d) of 3.0 g (10.1 mmol) was dispersed in pyridine of 40 ml and toluene of 20 ml, thereto was added phosphorous oxychloride of 0.5 g and the mixture was reacted further for 4 hrs at room temperature. After completing the reaction, ethyl acetate was added to the reaction mixture, which was then washed and concentrated. The resulting residue was refined by the use of column chromatography and recrystalized in a mixture of acetonitrile and ethyl acetate to obtain objective Compound (1) of 1.95 g in a 33% yield. The melting point of the product obtained was 138° to 140° C. and the structure thereof was confirmed by $^1$H-NMR, IR and Mass spectrum.

Other couplers of the invention can be synthesized in a manner similar to the above method. The inventive coupler is used in an amount of $1 \times 10^{-3}$ to 1 mol per mol of silver halide, preferably, $1 \times 10^{-2}$ to $8 \times 10^{-1}$ mol per mol of silver halide. The coupler may be used in combination with another kind of a cyan coupler.

To the inventive coupler, there can be applied a method or technique used in a conventional dye forming coupler.

The coupler of the present invention can be employed as a dye-forming material for use in any type of color photography. As embodiments thereof are cited coupler-in developer type dye formation and coupler-in-emulsion type dye formation. In the case when used in the coupler-in-developer type dye formation, the coupler of the invention is dissolved in an aqueous alkaline solution or organic solvent such as an alcohol and added to a developer to be used.

In the case when used in the coupler-in-emulsion type dye formation, the coupler of the invention is incorporated in a photographic light sensitive element.

In a preferred embodiment thereof, the inventive coupler is incorporated in a silver halide emulsion and the emulsion is coated on a support to prepare a color photographic light sensitive material.

The coupler of the present invention can be used for a color photographic light sensitive material such as negative-working or positive-working film, or color print paper.

The color photographic light sensitive material including a color print paper in which the inventive coupler is used may be used for monocolor or multicolor. In a multicolor photographic material, the inventive coupler may be incorporated in any layer thereof and conventionally, the coupler is contained in green-sensitive silver halide emulsion layer and/or red-sensitive silver halide emulsion layer. The multicolor photographic light sensitive material comprises dye image forming units which are respectively sensitive to the spectral ranges of three primary colors. Each of the image forming units comprises one or more silver halide emulsion layers sensitive to a spectral range. Constituting layers of the photographic material including the image forming units can be arranged in various orders as known in the photographic art.

A representative multicolor photographic light sensitive material comprises a support having thereon a cyan dye image forming unit comprising a red-sensitive silver halide emulsion layer containing a cyan dye-forming coupler, a magenta dye image forming unit comprising a green-sensitive silver halide emulsion layer containing a magenta dye-forming coupler and a yellow dye image forming unit comprising a blue-sensitive silver halide emulsion layer containing a yellow dye-forming coupler, in which at least one of the cyan and/or magenta dye-forming couplers is a coupler of the present invention.

The photographic light sensitive material may further have an additional layer such as a filter layer, interlayer, protective layer, sublayer or under-coat layer.

The coupler of the present invention can be contained in a silver halide emulsion layer according to a method known in the art. Exemplarily, the inventive coupler is, singly or in combination, dissolved in a high boiling organic solvent having a boiling point of 175° C. or higher such as tricresyl phosphate or dibutyl phthalate, a low boiling solvent such as butyl acetate or butyl propionate, or a mixture thereof; the resulting solution is mixed with a aqueous gelatin solution containing a surfactant to be emulsified with a high speed mixer or colloid mill and the resulting dispersion is added into a silver halide emulsion to obtain an emulsion used for the present invention.

Silver halide employed in the photographic light sensitive material containing the inventive coupler is preferably silver chloride, silver chlorobromide or silver iodochlorobromide. A mixture such as a blend of silver chloride and silver bromide may be employed. In the case when used for a color print paper, a silver halide emulsion is desired to have a high developability so that the silver halide emulsion grains contain preferably chloride; and silver chloride, or 1% or more chloride-containing silver chlorobromide or silver iodochlorobromide is preferable.

The silver halide emulsion can be chemically sensitized in accordance with conventional methods. The emulsion can be also spectrally sensitized to a desired spectral region.

In order to prevent fogging occurred during the course of manufacture, storage or photographic processing thereof or to stabilize the photographic performance thereof, a compound known as a fog restrainer or stabilizer can be added to the silver halide emulsion.

Into a color photographic light sensitive material containing the inventive coupler, there can be incorporated various additives such as anticolor-stain agent, dye image stabilizer, UV absorbent, antistatic agent, matting agent and surfactant.

These compounds are referred to, for example, Research Disclosure Vol. 176, pages 22–31 (Dec. 1978).

The color photographic light sensitive material containing the inventive coupler is color-developed according to the manner known in the art to form a color image.

The color photographic light sensitive material containing the inventive coupler may contain a color developing agent or a precursor thereof in a hydrophilic colloidal layer, which is processed in an alkaline activator bath.

The color photographic light sensitive material containing the inventive coupler is, after color-developing, further subjected to bleaching and fixing. Bleaching and fixing may be conducted simultaneously.

It is conventional that, after fixing, the photographic material is subjected to washing. Stabilization may be conducted in place of washing or in combination thereof.

EXAMPLES

The present invention will be exemplarily explained as below but the invention is not limited thereto.

Example 1

On a paper support laminated on both sides with polyethylene, the following layers were coated in this order from the support to prepare a red-sensitive color photographic light sensitive material Sample 1. Unless otherwise noted, the addition amount of a compound is expressed in per $m^2$ of the photographic material. The amount of silver halide was converted to that of silver.

1st layer: Emulsion layer

A red-sensitive emulsion layer comprises gelatin of 1.3 g, a red-sensitive silver bromochloride emulsion (containing 99.5 mol % silver chloride) of 0.21 mol and a comparative cyan coupler a of $9.1 \times 10^{-4}$ mol dissolved in dioctyl phthalate of 0.45 g.

2nd layer: Protective layer

A protective layer comprises gelatin of 0.50 g, in which a hardener, 2,4-dichloro-6-hydroxy-s-triazine sodium salt was added in an amount of 0.017 g per g of gelatin.

Further, inventive Samples 2 to 8 were prepared in the same manner as Sample 1, except that a comparative coupler a was replaced by an equimolar amount of a coupler as shown in Table 1.

Thus prepared Samples 1 to 8 were exposed through an optical wedge according in a conventional manner and processed according to the following steps.

The processing condition is as follows.

| Processing step | Temperature | Time |
| --- | --- | --- |
| Color developing | 35.0 ± 0.3° C. | 45 sec. |
| Bleach-fixing | 35.0 ± 0.5° C. | 45 sec. |
| Stabilizing | 30 to 34° C. | 90 sec. |
| Drying | 60 to 80° C. | 60 sec. |

| Color developer | |
| --- | --- |
| Water | 800 ml |
| Triethanolamine | 10 g |
| N,N-Diethylhydroxylamine | 5 g |
| Potassium bromide | 0.02 g |
| Potassium chloride | 2 g |
| Potassium sulfite | 0.3 g |
| 1-Hydroxyethylidene-1,1-diphosphonic acid | 1.0 g |
| Ethylenediaminetetraacetic acid | 1.0 g |
| Disodium catechol-3,5-disulfonate | 1.0 g |
| Diethylene glycol | 10 g |
| N-Ethyl-N-β-methnesulfonamidoethyl-3-methyl-4-aminoaniline sulfate | 4.5 g |
| Brightener (4,4'-diaminostilbene sulfonic acid derivative) | 1.0 g |
| Potassium carbonate | 27 g |

Water was added to make 1 liter in total and the pH was adjusted to 10.10.

| Bleach-fixer | |
| --- | --- |
| Ferric ammonium ethylenediaminetetraacetate dihydride | 60 g |
| Ethylenediaminetetraacetic acid | 3 g |
| Ammonium thiosulfate (70% aq. solution) | 100 ml |
| Ammonium sulfite (40% aq. solution) | 27.5 ml |

Water was added to make 1 liter in total and the pH was adjusted to 5.7.

| Stabilizer | |
| --- | --- |
| 5-Chloro-2-methyl-4-isothiazoline-3-one | 0.2 g |
| 1,2-Benzisothiazoline-3-one | 0.3 g |
| Ethylene glycol | 1.0 g |
| 1-Hydroxyethylidene-1,1-diphosphonic acid | 2.0 g |
| o-Phenylphenol sodium salt | 1.0 g |
| Ethylenediaminetetraacetic acid | 1.0 g |
| Ammonium hydroxide (20% aq. solution) | 3.0 g |
| Brightener (4,4'-diaminostilbene sulfonic acid derivative) | 1.5 g |

Water was added to make 1 liter in total and the pH was adjusted to 7.0 with sulfuric acid or potassium hydroxide.

Samples 1 to 8 thus-processed were sensitometrically measured with respect to a maximum density (Dmax) using a densitometer (Type KD-7, product of Konica), and after processed samples were allowed to stand for 21 days under the condition of a high temperature and humidity (85° C., 60% R.H.), the samples were evaluated with respect to heat stability of the dye image. The heat stability was shown as percentage of residual density of the image having an initial density of 1.0 (residual dye ratio).

Comparative coupler a

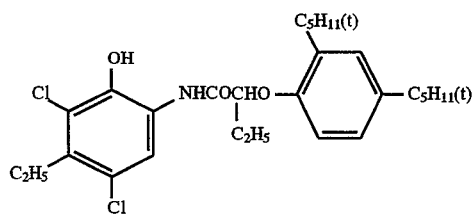

Comparative coupler b

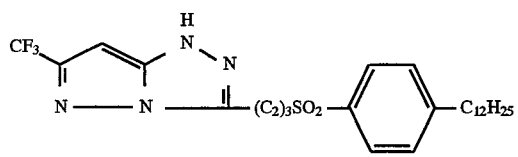

(Coupler as described in JP-A 64-554/1989)

TABLE 1

| Sample No. | Coupler | Dmax | Residual dye ratio (%) |
| --- | --- | --- | --- |
| 1 | Comp. a | 2.30 | 81 |
| 2 | Comp. b | 1.79 | 94 |
| 3 | Inv. (1) | 2.49 | 99 |
| 4 | Inv. (5) | 2.52 | 100 |
| 5 | Inv. (11) | 2.58 | 99 |
| 6 | Inv. (14) | 2.44 | 98 |
| 7 | Inv. (19) | 2.40 | 99 |
| 8 | Inv. (21) | 2.51 | 98 |

As can be seen from Table 1, samples containing an inventive coupler were proved to be high in Dmax and the residual dye ratio, and excellent in dye formation and tropical heat stability.

Example 2

Using a paper support laminated with polyethylene on one side thereof and on another side laminated with polyethylene containing titanium dioxide, the following layers were coated on the titaniumdioxide-containing side to prepare a silver halide color photographic light sensitive material (Sample 9). Coating solutions were prepared in the following manner.

To a yellow coupler (Y-1) of 26.7 G, dye image stabilizer (ST-1) of 10.0 G, dye image stabilizer (ST-2) of 6.67 G, additive (HQ-1) of 0.67 G, anti-irradiation dye (AI-3) and high boiling solvent (DNP) of 6.67 g, there was added ethyl acetate of 60 ml, and the resulting solution was dispersed in 220 ml of an aqueous 20% gelatin solution containing surfactant (SU-1) of 7 ml to prepare a yellow coupler dispersion. This dispersion was mixed with a blue-sensitive silver halide emulsion prepared according to the condition described below to prepare a coating solution for the 1st layer.

Coating solutions for the 2nd layer through the 7th layer were prepared in a manner similar to the 1st layer coating solution.

In addition, a hardener (H-1) was added to the 2nd and 4th layers, and hardener (H-2) was added to the 7th layer. As a coating aid were added surfactants (SU-2 and SU-3) to make adjustment of a surface tension. Unless otherwise noted, the amount to be added to the silver halide photographic material was expressed in g per $m^2$. The amount of silver halide was converted to that of silver.

| | |
|---|---|
| 7th Layer (protective layer) | |
| Gelatin | 1.00 (g/m$^2$) |
| DIDP | 0.005 |
| Additive (HQ-2) | 0.002 |
| Additive (HQ-3) | 0.002 |
| Additive (HQ-4) | 0.004 |
| Additive (HQ-5) | 0.02 |
| Compound (F-1) | 0.002 |
| 6th Layer (UV absorbing layer) | |
| gelatin | 0.40 |
| UV absorbent (UV-1) | 0.10 |
| UV absorbent (UV-2) | 0.04 |
| UV absorbent (UV-3) | 0.16 |
| Additive (HQ-5) | 0.04 |
| DNP | 0.20 |
| PVP | 0.03 |
| Anti-irradiation dye AI-2) | 0.02 |
| Anti-irradiation dye (AI-4) | 0.01 |
| 5th Layer (red-sensitive layer) | |
| Gelatin | 1.30 |
| Red-sensitive silver bromochloride (Em-R) | 0.21 |
| Cyan coupler (C-1) | 0.17 |
| Cyan coupler (C-2) | 0.25 |
| Dye image stabilizer (ST-1) | 0.20 |
| Additive (HQ-1) | 0.01 |
| HBS-1 | 0.20 |
| DOP | 0.20 |
| 4th Layer (UV absorbing layer) | |
| Gelatin | 0.94 |
| UV absorbent (UV-1) | 0.28 |
| UV absorbent (UV-2) | 0.09 |
| UV absorbent (UV-3) | 0.38 |
| Additive (HQ-5) | 0.10 |
| DNP | 0.40 |
| 3rd Layer (green-sensitive layer) | |
| Gelatin | 1.40 |
| Green-sensitive silver bromochloride (Em-G) | 0.17 |
| Magenta coupler (M-1) | 0.23 |
| Dye image stabilizer (ST-3) | 0.20 |
| Due image stabilizer (ST-4) | 0.17 |
| DIDP | 0.13 |
| DBP | 0.13 |
| Anti-irradiation dye (AI-1) | 0.01 |
| 2nd Layer (interlayer) | |
| Gelatin | 1.20 |
| Additive (HQ-2) | 0.03 |
| Additive (HQ-3) | 0.03 |
| Additive (HQ-4) | 0.05 |
| Additive (HQ-5) | 0.23 |
| DIDP | 0.06 |
| Compound (F-1) | 0.002 |
| 1st Layer (blue-sensitive layer) | |
| Gelatin | 1.20 |
| Blue-sensitive silver bromochloride (Em-B) | 0.26 |
| Yellow coupler (Y-1) | 0.80 |
| Dye image stabilizer (ST-1) | 0.30 |
| Dye image stabilizer (ST-2) | 0.20 |

-continued
| | |
|---|---|
| Additive (HQ-1) | 0.02 |
| Anti-radiation dye (AI-3) | 0.01 |
| DNP | 0.20 |
| Support | |
| Polyethylene-laminated paper | |
Y-1
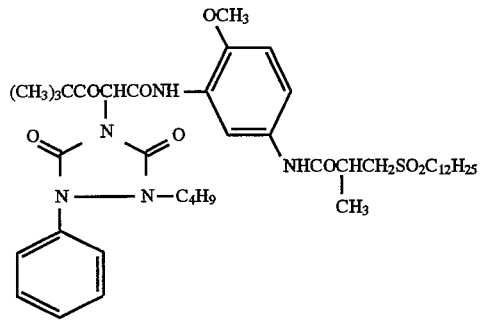
M-1
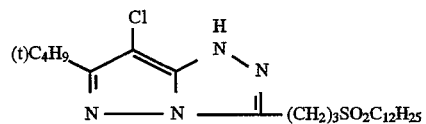
C-1
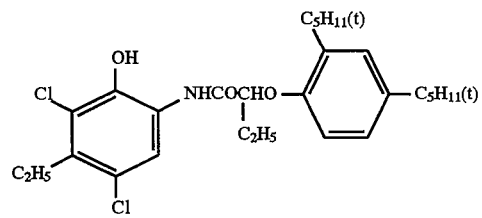
C-2
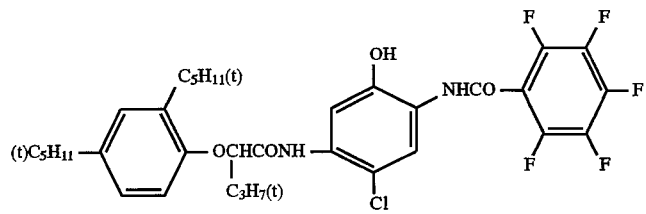
ST-1
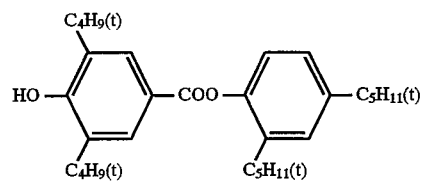
ST-2
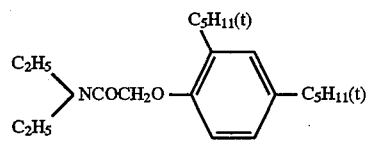
ST-3
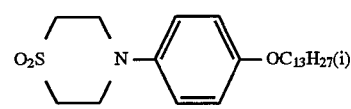
ST-4
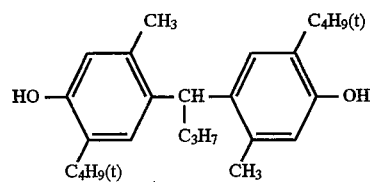

UV-1 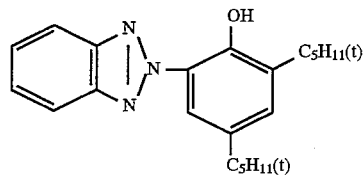
UV-2 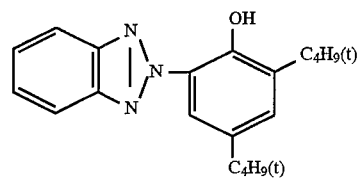
UV-3 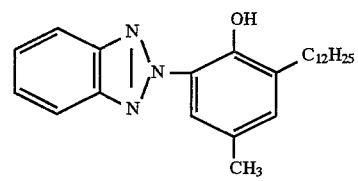
DBP: Dibuthyl phthalate
DOP: Dioctylphthalate
DNP: Dinonyl phthalate
DIDP: Diisodecylphthalate
PVP: Polyvinylpyrroridone
HQ-1 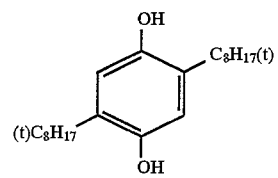
HQ-2 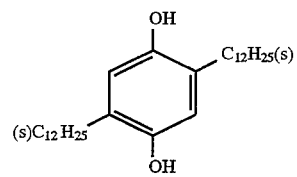
HQ-3 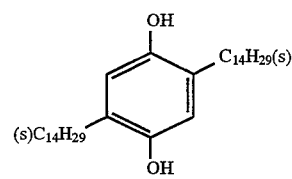
HQ-4 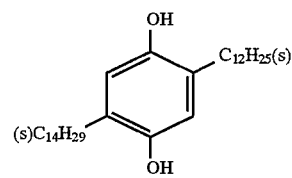
HQ-5 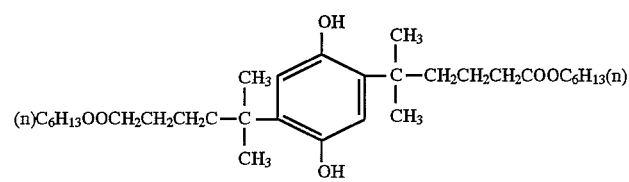

-continued
HBS-1 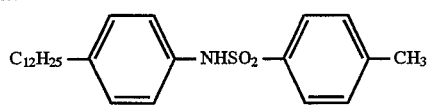
AI-1 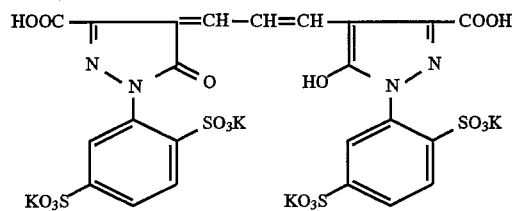
AI-2 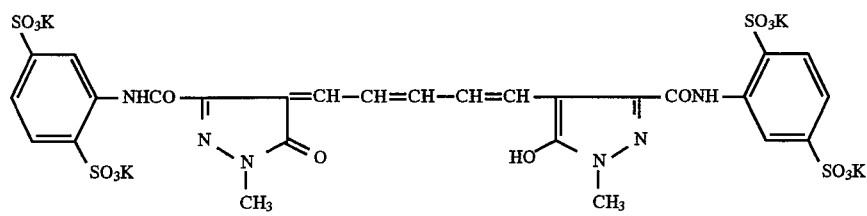
AI-3 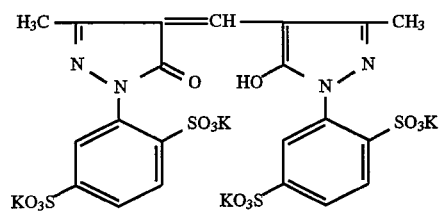
AI-4 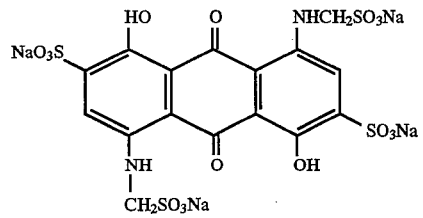
SU-1 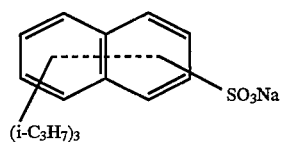
SU-2 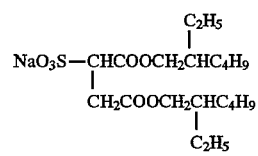
SU-3 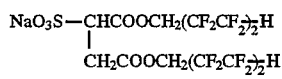
H-1 $C(CH_2SO_2CH=CH_2)_4$
H-2 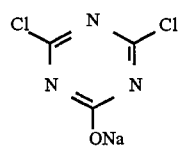

F-1 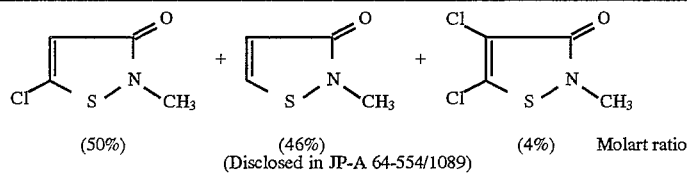

(50%)     (46%)     (4%)    Molar ratio
(Disclosed in JP-A 64-554/1089)

Preparation of a blue-sensitive silver halide emulsion:

To 1000 ml of a 2% gelatin aqueous solution maintained at 40° C. were simultaneously added solutions A and B for a period of 30 min., while being controlled at a pAg of 6.5 and pH of 3.0, and then solutions C and D were simultaneously added for a period of 180 min., while being controlled at a pAg of 7.3 and pH of 5.5. The pH was controlled with an aqueous solution of sulfuric acid or sodium hydroxide. The pAg was controlled with a mixed halide solution comprising chloride and bromide in a molar ratio of 99.8:0.2, of which concentration was 0.1 mol/liter when solutions A and B were mixed and 1 mol/liter, when solutions C and D were mixed.

| Solution A | |
|---|---|
| Sodium chloride | 3.42 g |
| Potassium bromide | 0.03 g |
| Water to make | 200 ml |
| Solution B | |
| Silver nitrate | 10 g |
| Water to make | 200 ml |
| Solution C | |
| Sodium chloride | 102.7 g |
| Potassium bromide | 1.0 g |
| Water to | 600 ml |
| Solution D | |
| Silver nitrate | 300 g |
| Water to make | 600 ml |

After completing addition, the emulsion was desalted using an aqueous 5% solution of Demol N (product of Kao/Atlas) and 2% magnesium sulfate solution and then was further mixed with an aqueous gelatin solution to obtain a monodispersed, silver bromochloride cubic grain emulsion (EMP-1) having an average grain size (F) of 0.85 μm, a variation coefficient of grain size (σ/F) of 0.07 and chloride content of 99.5 mol %.

The emulsion (EMP-1) was chemically sensitized at 50° C. for 90 min. using the following compounds to obtain a blue-sensitive silver halide emulsion (Em-B).

| Sodium thiosulfate | 0.8 mg/mol AgX |
|---|---|
| Chloroauric acid | 0.5 mg/mol AgX |
| Stabilizer STAB-1 | $6 \times 10^{-4}$ mol/mol AgX |
| Sensitizing dye BS-1 | $4 \times 10^{-4}$ mol/mol AgX |
| Sensitizing dye BS-2 | $1 \times 10^{-4}$ mol/mol AgX |

Preparation of green-sensitive silver halide emulsion:

A monodispersed, cubic silver bromochloride grain emulsion (EMP-2) having an average grain size (F) of 0.43 μm, a variation coefficient of grain size (σ/F) of 0.08 and chloride content of 99.5 mol % was prepared in the same manner as emulsion (EMP-1), except that the addition time of solutions A and B, and the addition time of solutions C and D were respectively varied.

The emulsion (EMP-2) was chemically sensitized at 55° C. for 120 min. using the following compounds to obtain a green-sensitive silver halide emulsion (Em-G).

| Sodium thiosulfate | 1.5 mg/mol AgX |
|---|---|
| Chloroauric acid | 1.0 mg/mol AgX |
| Stabilizer STAB-1 | $6 \times 10^{-4}$ mol/mol AgX |
| Sensitizing dye GS-1 | $4 \times 10^{-4}$ mol/mol AgX |

Preparation of red-sensitive silver halide emulsion:

A monodispersed, cubic silver bromochloride grain emulsion (EMP-3) having an average grain size (F) of 0.50 μm, a variation coefficient of grain size (σ/F) of 0.08 and chloride content of 99.5 mol % was prepared in the same manner as emulsion (EMP-1), except that the addition time of solutions A and B, and the addition time of solutions C and D were respectively varied.

The emulsion (EMP-3) was chemically sensitized at 60° C. for 900 min. using the following compounds to obtain a red-sensitive silver halide emulsion (Em-R).

| Sodium thiosulfate | 1.8 mg/mol AgX |
|---|---|
| Chloroauric acid | 2.0 mg/mol AgX |
| Stabilizer STAB-1 | $6 \times 10^{-4}$ mol/mol AgX |
| Sensitizing dye RS-1 | $1 \times 10^{-4}$ mol/mol AgX |

The variation coefficient was determined from a standard deviation (σ) and average grain size (r), based on the following relation, $$\sigma = \sqrt{\frac{\Sigma (\gamma_i - \bar{\gamma})^2}{\Sigma_i n_i}}$$

wherein $r_i$ represents a grain size and $n_i$ represents the number of grains having a grain size of $r_i$.

BS-1 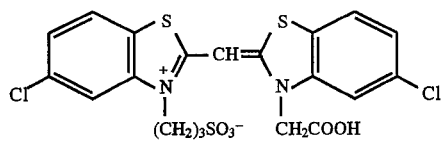

BS-2 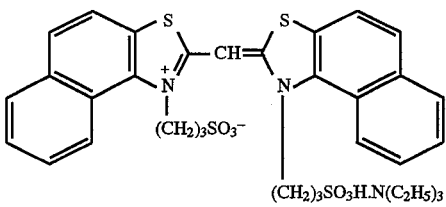

GS-1 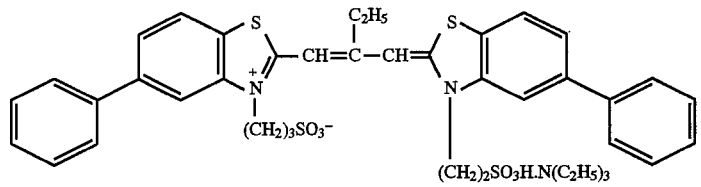

RS-1 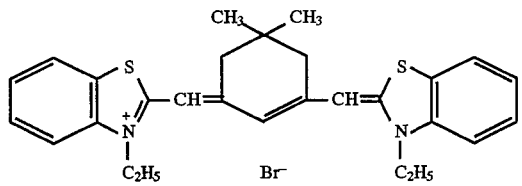

STAB-1 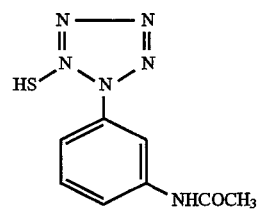

Samples 10 to 22 were prepared in the same manner as in Sample 9, except that cyan couplers C-1 and C-2 were replaced by a coupler as shown in Table 2, in an amount equivalent to that of C-1 and C-2 in total.

Thus prepared samples were exposed and processed in a manner similar to Example 1, and sensitometrically measured with respect to the maximum density (Dmax) of the red-sensitive layer.

Further, with respect to color reproduction, samples were evaluated in the following maner.

First, a Macbeth Color Checker (product of Macbeth Corp.) was photographed using a color negative film (Konica Color LV-400, product of Konica) and a camera (Konica FT-1 MOTOR, product of Konica). The film photographed was subjected to processing for a color negative film (CNK-4, product of Konica) and, using a printer (Konica Color Printer CL-P 2000, product of Konica), the resulting negative image was printed on each of Samples 9 to 22 in size of 82 mm×117 mm to obtain a print. When being printed, the printer was adjusted so that neutral gray of the checker is reproduced in neutral gray of the print.

Prints thus-obtained were each visually evaluated with respect to color reproduction and blackness (black tone). The color reproduction was evaluated based on five grades, 1 (poor) to 5 (excellent).

Results thereof are shown in Table 2.

TABLE 2

| Sample No. | Cyan coupler | Dmax | Color reproduction | | | Blackness | Remarks |
|---|---|---|---|---|---|---|---|
| | | | Cyan | Blue | Green | | |
| 9 | C-1/C-2 | 2.49 | 3 | 3 | 3 | Ex.* | Comp. |
| 10 | c | 2.10 | 3 | 5 | 3 | Is. | Comp. |
| 11 | d | 2.27 | 3 | 5 | 3 | Is. | Comp. |
| 12 | (1) | 2.54 | 5 | 5 | 5 | S. | Inv. |
| 13 | (4) | 2.58 | 4 | 5 | 5 | S. | Inv. |
| 14 | (9) | 2.53 | 5 | 5 | 5 | S. | Inv. |
| 15 | (13) | 2.49 | 5 | 5 | 5 | S. | Inv. |
| 16 | (18) | 2.49 | 5 | 5 | 5 | S. | Inv. |
| 17 | (24) | 2.59 | 5 | 5 | 5 | S. | Inv. |
| 18 | (28) | 2.48 | 5 | 5 | 5 | S. | Inv. |
| 19 | (29) | 2.54 | 5 | 5 | 5 | S. | Inv. |
| 20 | (30) | 2.41 | 3 | 5 | 5 | S. | Inv. |
| 21 | (32) | 2.42 | 3 | 5 | 5 | S. | Inv. |
| 22 | (33) | 2.40 | 3 | 5 | 5 | S. | Inv. |

TABLE 2-continued

| Sample No. | Cyan coupler | Dmax | Color reproduction | | | Black-ness | Re-marks |
|---|---|---|---|---|---|---|---|
| | | | Cyan | Blue | Green | | |

Comparative coupler c (n)C₁₀H₂₁NHCO— structure —NHSO₂C₁₈H₃₇

(Disclosed in JP-A 63-250650/1988)

Comparative coupler d (C₄H₉)₂NCO— structure —NHCOC₁₃H₂₇

(Disclosed in JP-A 64-554/1089)

*Ex.: Excellent, S.: Sufficient, Is.: Insufficient (Disclosed in JP-A 64-554/1089)

As can be seen from The 2, Sample 9, which contains comparative couplers C-1 and C-2 was remarkably insufficient in color reproduction. Samples 10 and 11, which contains each Comparative couplers c and d resulted in improvement in blue-color reproduction. However, each of the led to no improvement in cyan or green color reproduction and was insufficient in blackness due to a low maximum density thereof.

Contrarily to that, Samples 12 to 22 which contain each the inventive couple achieved improvements in any of cyan, blue and green color reproductions, and high in dye forming property (Dmax) and excellent in blackness.

What is claimed is:

1. A multicolor silver halide photographic light sensitive material comprising a support having thereon a cyan dye-forming unit comprised of at least one red sensitive silver halide emulsion layer containing a cyan dye-forming coupler represented by the following formula (I) or (II),

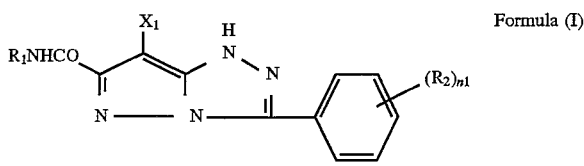

Formula (I)

-continued

Formula (II)

wherein $R_1$ and $R_3$ represents a substituted or branched alkyl group having 1 to 32 carbon atoms or a cycloalkyl group; $R_2$ and $R_4$ represents a hydrogen atom or a substituent; $X_1$ and $X_2$ represents a hydrogen atom or a group capable of being split off upon reaction with an oxidation product of a color developing agent; and $n_1$ and $n_2$ are each an integer of 1 to 5, a magenta dye image-forming unit comprised of at least one green-sensitive silver halide emulsion layer containing a magenta dye-forming coupler, and a yellow dye image-forming unit comprised of at least one blue-sensitive silver halide emulsion layer containing a yellow dye-forming coupler.

2. The photographic material of claim 1, wherein said cyan coupler is contained in an amount of $1 \times 10^{-3}$ to 1 mol per mol of silver halide.

3. The photographic material of claim 1, wherein said silver halide emulsion layer further contains silver halide grains comprising silver chloride, silver chlorobromide or silver iodochlorobromide.

* * * * *